United States Patent [19]

Adachi et al.

[11] 4,232,114
[45] Nov. 4, 1980

[54] COLOR PHOTOGRAPHIC LIGHT-SENSITIVE ELEMENTS CONTAINING ANTI-COLOR FOGGING AGENTS

[75] Inventors: Keiichi Adachi; Tadao Shishido; Akio Mitsui, all of Ashigara, Japan

[73] Assignee: Fuji Photo Film Co., Ltd., Ashigara, Japan

[21] Appl. No.: 939,108

[22] Filed: Sep. 1, 1978

Related U.S. Application Data

[63] Continuation-in-part of Ser. No. 800,817, May 26, 1977, abandoned.

[30] Foreign Application Priority Data

May 31, 1976 [JP] Japan .................................. 51-63099

[51] Int. Cl.$^2$ .............................................. G03C 1/76
[52] U.S. Cl. .................................... 430/504; 430/551; 430/362; 430/372
[58] Field of Search ....................... 96/56, 95, 22, 109, 96/76, 74 R

[56] References Cited

U.S. PATENT DOCUMENTS

| 2,701,197 | 2/1955 | Thirtle et al. | 96/56 |
|---|---|---|---|
| 2,732,300 | 1/1956 | Thirtle et al. | 96/56 |
| 3,930,866 | 1/1976 | Oishi et al. | 96/56 |
| 3,935,016 | 1/1976 | Nishimura et al. | 96/56 |
| 3,948,663 | 4/1976 | Shiba et al. | 96/22 |

*Primary Examiner*—Mary F. Downey
*Attorney, Agent, or Firm*—Sughrue, Rothwell, Mion, Zinn and Macpeak

[57] ABSTRACT

A color photographic light-sensitive element having (1) reduced fog, (2) low reduction in sensitivity and (3) good yellow dye image light fastness, and comprising a support having thereon at least one silver halide photographic emulsion and optionally one or more non-light-sensitive subsidiary layers, wherein a blue-sensitive silver halide photographic emulsion layer and/or a non-light-sensitive layer adjacent thereto contains at least one asymmetrical hydroquinone compound selected from the group consisting of 2-methyl-5-tert-octylhydroquinone, 2-tert-butyl-5-tert-amylhydroquinone, 2-tert-butyl-5-tert-hexylhydroquinone, 2-methyl-5-tert-hexylhydroquinone, 2-methyl-5-tert-amylhydroquinone, 2-methyl-5-(1'-methylcyclohexyl)hydroquinone and precursors thereof wherein either or both hydroxyl groups are modified with an acyl group represented by the formulae:

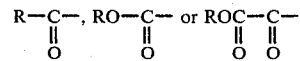

wherein R represents an alkyl group.

11 Claims, No Drawings

COLOR PHOTOGRAPHIC LIGHT-SENSITIVE ELEMENTS CONTAINING ANTI-COLOR FOGGING AGENTS

CROSS-REFERENCE TO RELATED APPLICATIONS

This application is a continuation-in-part application of Ser. No. 800,817, filed May 26, 1977, now abandoned.

BACKGROUND OF THE INVENTION

1. Field of the Invention

The present invention relates to a color photosensitive element in which color fogging (or color stain) is reduced without reduction in sensitivity and the light fastness of a yellow dye image formed is improved, and more particularly, to a silver halide color photosensitive element containing an asymmetrical hydroquinone compound which has sufficient solubility in a solvent.

2. Description of the Prior Art

It is well known that color fog arises in a color photosensitive element of the type which has a silver halide photosensitive emulsion layer containing a color-forming coupler and which is developed with a color developing agent such as p-phenylenediamines. Methods for preventing the formation of color fog using a variety of alkyl hydroquinones have been proposed for a long time.

For instance, mono-straight chain alkyl hydroquinones are disclosed in U.S. Pat. No. 2,728,659, Japanese Patent Application (OPI) No. 106,329/74, etc. In addition, mono-branched chain alkyl hydroquinones are disclosed in U.S. Pat. No. 3,700,453, West German Patent Application (OLS) No. 2,149,789, Japanese Patent Application (OPI) Nos. 156,438/75 and 106,329/74. On the other hand, di-straight chain alkyl hydroquinones are disclosed in U.S. Pat. Nos. 2,728,659 and 2,732,300 (equivalent to British Pat. No. 752,147), British Pat. Nos. 752,146 and 1,086,208 and *Chemical Abstracts*, Vol. 58, 6367h (1963) and, in addition, di-branched chain alkyl hydroquinones are disclosed in U.S. Pat. Nos. 3,700,453 and 2,732,300, British Pat. No. 1,086,208, *Chemical Abstracts*, Vol. 58, 6367h (1963), Japanese Patent Application (OPI) No. 156,438/75, Japanese Patent Publication No. 21,249/75, etc.

Other examples of alkyl hydroquinones as an anti-color fogging agent are disclosed in British Pat. Nos. 558,258, 557,750 (equivalent to U.S. Pat. No. 2,360,290), 557,802 and 731,301 (equivalent to U.S. Pat. No. 2,701,197), U.S. Pat. Nos. 2,336,329, 2,403,721 and 3,582,333 and West German Patent Application (OLS) No. 2,505,016 (equivalent to Japanese Patent Application (OPI) No. 110,337/75).

Furthermore, known hydroquinone compounds as anti-color fogging agents are known to deteriorate the light-fastness of a dye image formed by reaction between a color coupler and an oxidation product of an aromatic primary amine developer, in particular, to deteriorate the light-fastness of a yellow dye image formed.

Accordingly, it has been desired in producing color photosensitive elements to develop a novel anti-color fogging agent which prevents more effectively color fogging without a deterioration of the photographic sensitivity and, in addition, sufficiently dissolves in a solvent and, moreover, improves the light fastness of the dye image formed by color development, so that a higher quality color photograph can be obtained.

SUMMARY OF THE INVENTION

An object of the present invention is, therefore, to provide a color photographic light-sensitive element containing a novel anti-color fogging agent which is capable of preventing more effectively color fogging without a deterioration of the photographic sensitivity and a deterioration of the light fastness of a yellow dye image formed.

In addition, another object of the present invention is to provide a color photographic light-sensitive element containing such a novel anti-color fogging agent which is sufficiently soluble in a solvent.

These objects are effectively accomplished by a color photographic light-sensitive element comprising a support having thereon at least one silver halide photographic emulsion and, optionally one or more non-light-sensitive subsidiary layers wherein a blue-sensitive silver halide photographic emulsion layer and/or a non-light-sensitive layer adjacent thereto contains at least one asymmetrical hydroquinone compound selected from the group consisting of 2-methyl-5-tert-octylhydroquinone, 2-tert-butyl-5-tert-amylhydroquinone, 2-tert-butyl-5-tert-hexylhydroquinone, 2-methyl-5-tert-hexylhydroquinone, 2-methyl-5-tert-amylhydroquinone, 2-methyl-5-(1'-methylcyclohexyl)hydroquinone and precursors thereof wherein either or both hydroxyl groups are modified with an acyl group represented by the formulae:

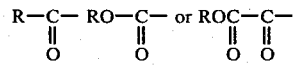

wherein R represents an alkyl group.

DETAILED DESCRIPTION OF THE INVENTION

In the above description, the term "precursor" means a compound which forms the hydroquinone compound upon hydrolysis. Examples of precursors include hydroquinones having therein one or two hydroxy groups modified with an acyl group or the like (the term "acyl group" is used in this aspect in a broad sense, with examples of acyl groups include an

group, an

group and an

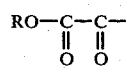

group wherein R represents an aliphatic group such as an alkyl group).

The employment of asymmetric hydroquinone compounds as an anti-color fogging agent is generally disclosed in *Chemical Abstracts*, Vol. 58, 6367h (1963), U.S. Pat. Nos. 2,701,197, 2,732,300 and 3,582,333 and Japanese Patent Application (OPI) No. 156,438/75. However, these compounds which are specifically taught therein can be classified into three groups: (1) asymmetric alkyl hydroquinones containing a tertiary alkyl group and a secondary alkyl group, (2) asymmetric alkyl hydroquinones containing a secondary alkyl group and a methyl group, and (3) asymmetric alkyl hydroquinones having a methyl group and a halogen atom.

Consequently, it could not be expected from the teachings of the prior art as referred to above that the asymmetric hydroquinone compounds having the specific structure as set forth when used in the present invention would provide the excellent and unexpected effects obtained.

The anti-color fogging agent of the present invention may be used individually, as a combination of two or more thereof or in a combination with other hydroquinone derivative(s) as disclosed in the prior art referred to hereinbefore.

Specific examples of anti-color fogging agents which can be used in the present invention can be represented by the following structural formulae:

2-Methyl-5-tert-octylhydroquinone
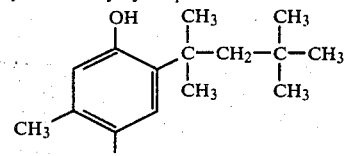
(1)

2-Methyl-5-tert-hexylhydroquinone
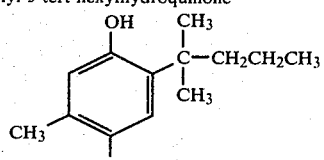
(2)

2-Methyl-5-tert-amylhydroquinone
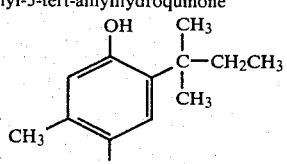
(3)

2-tert-Butyl-5-t-amylhydroquinone
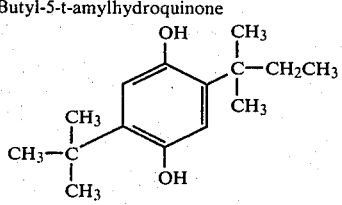
(4)

2-tert-Butyl-5-tert-hexylhydroquinone
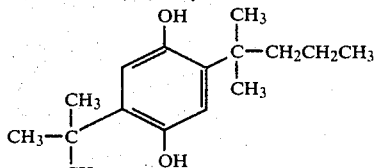
(5)

2-Methyl-5-(1'-methylcyclohexyl)hydroquinone

-continued
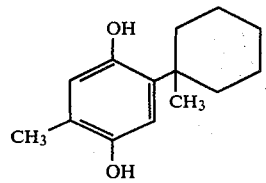
(6)

The following synthesis examples are given to illustrate the synthesis of representative examples of the hydroquinones used in the present invention. Unless otherwise indicated herein, all parts, percents, ratios and the like are by weight.

SYNTHESIS EXAMPLE 1

Compound (1)

To a solution of 24.8 g of toluhydroquinone in 30 ml of methanol was added 33.6 g of diisobutylene and then 16 ml of concentrated sulfuric acid (36 N) was added dropwise at a controlled temperature of 40° to 50° C. with stirring and subsequently the reaction was further continued in this temperature range for 5 hours. The thus-obtained reaction mixture was cooled and then 200 ml of water and 200 ml of benzene were added thereto. The benzene layer which separated was washed with water and then the benzene solution was collected using a fractionating funnel. Next, benzene was distilled off from the solution and to the residual oil so obtained was added 200 ml of n-hexane for crystallization. The thus-obtained crystals were collected by filtration, dried and then recrystallized from a mixed solvent of benzene and hexane (1:10 by volume). Thus, 27 g of Compound (1) having a melting point of 89° C. was obtained.

SYNTHESIS EXAMPLE 2

Compound (3)

To a solution of 24.8 g of t-butylhydroquinone and 42.9 g of t-amylalcohol in 50 ml of methanol was added dropwise 40 ml of concentrated sulfuric acid (36 N) at a controlled temperature of 30° to 35° C. with stirring. Then, the reaction was continued in this temperature range for 6 hours. To the reaction mixture were added 200 ml of water and 200 ml of benzene and thereafter a benzene layer separated. The benzene layer was sufficiently washed with water and then the benzene solution was separated by fractionation. Next, the benzene was distilled off from the solution and n-hexane was added to the residual oil so obtained for crystallization. As a result, 24 g of Compound (3) having a melting point of 85° to 87° C. was obtained.

SYNTHESIS EXAMPLE 3

Compound (6)

To a solution of 24.8 g of toluhydroquinone and 34.2 g of 2-methylcyclohexanol in 20 ml of ethanol was added dropwise 11 ml of concentrated sulfuric acid (36 N) at room temperature (about 20°–25° C.) and then the reaction was continued at a constant temperature of 70° to 75° C. for 5 hours. Next, to the reaction mixture were added 200 ml of benzene and 200 ml of water. The benzene layer separated thereafter was washed with water and then the benzene solution was recovered by fractionation. Then, the benzene was distilled off from the benzene solution, and n-hexane was added to the residual oil so obtained for crystallization. The thus-obtained crystals were collected by filtration, dried, and recrystallized from hexane. Thus, 10 g of Compound (6) having a melting point of 108° to 110° C. was obtained.

The anti-color fogging agent of the present invention can be incorporated into a blue-sensitive silver halide photographic emulsion layer and/or a non-light-sensitive layer adjacent the blue-sensitive silver halide photographic emulsion layer.

The color photosensitive element which can be used in the present invention is preferably a multilayer multicolor photosensitive element comprising a support having coated thereon three silver halide photographic emulsion layers each of which is sensitive to light in a different wavelength region. Such a color photosensitive element comprises a support having coated thereon a red-sensitive silver halide photographic emulsion layer containing a cyan color-forming coupler, a green-sensitive silver halide photographic emulsion layer containing a magenta color-forming coupler, a blue-sensitive silver halide photographic emulsion layer containing a yellow color-forming coupler and optionally one or more non-light-sensitive subsidiary layers such as a protective layer, a filter layer, an interlayer or an antihalation layer.

One preferred embodiment of the present invention is a color photographic light-sensitive element comprising a support having coated thereon a blue-sensitive silver halide photographic emulsion layer containing a yellow color-forming coupler and an asymmetrical hydroquinone compound used in the present invention, a green-sensitive silver halide photographic emulsion layer containing a magenta color-forming coupler and a red-sensitive silver halide photographic emulsion layer containing a cyan color-forming coupler, in this order from the support.

Another preferred embodiment of the present invention is a color photographic light-sensitive element comprising a support having coated thereon a red-sensitive silver halide photographic emulsion layer containing a cyan color-forming coupler, a green-sensitive silver halide photographic emulsion layer containing a magenta color-forming coupler and a blue-sensitive silver halide photographic emulsion layer containing a yellow color-forming coupler and an asymmetrical hydroquinone compound used in the present invention, in this order from the support.

Another preferred embodiment of the present invention is a color photographic light-sensitive element comprising a support having coated thereon a blue-sensitive silver halide photographic emulsion layer containing a yellow color-forming coupler and an asymmetrical hydroquinone compound used in the present invention, a red-sensitive silver halide photographic emulsion layer containing a cyan color-forming coupler and a green-sensitive silver halide photographic emulsion layer containing a magenta color-forming coupler, in this order from the support.

A non-light-sensitive subsidiary layer, such as a protective layer, a filter layer, an interlayer or an antihalation layer, which is adjacent the blue-sensitive silver halide photographic emulsion layer can also contain an asymmetrical hydroquinone compounds used in the present invention. Both a blue-sensitive silver halide photographic emulsion layer and non-light-sensitive layer adjacent thereto can contain an asymmetrical hydroquinone compound used in the present invention.

The asymmetrical hydroquinone compound used in the present invention, as an anti-color fogging agent, can be incorporated into a photosensitive element in the same manner as is conventionally used for the addition of color-forming couplers to the element.

The amount of the anti-color fogging agent employed depends upon factors such as the end-use of the photosensitive element, the dye image-forming couplers present, the silver halide photographic emulsion and the development processing. However, the anti-color fogging agent is generally used in an amount of about 0.1 to about 50 wt%, particularly, about 0.2 to about 20 wt%, based on the weight of the dye image-forming coupler with which it is employed in combination.

The photographic emulsion layer of the color photosensitive element which is used in the present invention contains a color coupler which is preferably a diffusion-resistant compound having in the molecule a hydrophobic group generally called a "ballast group". The coupler may be a four-equivalent color coupler or a two-equivalent color coupler, however, it is preferred for the coupler to be a two-equivalent color coupler, in particular. In addition, the photographic emulsion layer can contain a colored coupler for color correction or a coupler which releases a development inhibitor upon development (the so-called "DIR coupler"). The coupler may be a coupler which produces a colorless product as a result of the coupling reaction.

Open chain ketomethylene type couplers known in the art can be used as a yellow dye image-forming coupler. Of these couplers, benzoylacetanilide type compounds and pivaloylacetanilide type compounds are preferred. Specific examples of yellow dye image-forming couplers which can be used in the present invention are those as disclosed in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,213,461, 2,219,917, 2,261,361, 2,263,875, 2,414,006 and 2,406,087, and so on.

Of these yellow dye image-forming couplers, a two-equivalent benzoylacetanilide type coupler and a two-equivalent pivaloylacetanilide type coupler having a coupling-off group at the coupling position thereof are preferred. Examples of suitable coupling-off groups include an acyloxy group, a sulfonyloxy group, an aryloxy group, a urethane group, an imido group, a hydantoinyl group, an oxalidinedione group, a pyridine group and a pyridazone group. It is particularly preferred for the coupling-off group to be attached to the coupling position through a nitrogen atom, such as in a phthalimido group, a succinimido group, a 5,5-dimethyl-3-hydantoinyl group or a 2,4-oxazolidinedione group.

Pyrazolone type compounds, indazolone type compounds and cyanoacetyl compounds are used as a magenta dye image-forming coupler. Of these magenta couplers, pyrazolone type compounds are preferred. Specific examples of these magenta dye image-forming couplers which can be used in the present invention are those as disclosed in U.S. Pat. Nos. 2,600,788, 2,983,608, 3,062,653, 3,127,269, 3,062,653, 3,127,269, 3,311,476, 3,419,391, 3,519,429, 3,558,319, 3,582,322, 3,615,506, 3,834,908, 3,891,445 and 3,935,016, West German Pat. No. 1,810,464, West German Patent Application (OLS) Nos. 2,408,665, 2,417,945, 2,418,959 and 2,424,467, Japanese Patent Publication No. 6031/65, and so on.

Phenol type compounds and naphthol type compounds can be used as a cyan dye image-forming coupler. Specific examples of these cyan dye image-forming couplers are those as disclosed in U.S. Pat. Nos. 2,369,929, 2,434,272, 2,474,293, 2,521,908, 2,895,826, 3,034,892, 3,311,476, 3,458,315, 3,476,563, 3,583,971, 3,591,383 and 3,767,411, West German Patent Application (OLS) Nos. 2,414,830 and 2,454,329, Japanese Patent Application (OPI) No. 59838/73, and so on.

Examples of colored couplers which can be used are those as disclosed in, for example, U.S. Pat. Nos. 3,476,560, 2,521,908 and 3,034,892, Japanese Patent Publication Nos. 2016/69, 22335/63, 11304/67 and 32461/69, Japanese Patent Application No. 118029/75, and West German Patent Application (OLS) Nos. 2,418,959 and 2,538,323.

Examples of DIR couplers which can be used are those as disclosed in, for example, U.S. Pat. Nos. 3,227,554, 3,617,291, 3,701,783, 3,790,384 and 3,632,345, West German Patent Application (OLS) Nos. 2,414,006, 2,454,301 and 2,454,329, British Pat. No. 953,454, and Japanese Patent Application No. 146570/75.

The photosensitive element of the present invention can contain a compound which releases a development inhibiting agent other than a DIR coupler, and examples of these compounds are those as disclosed in, for example, U.S. Pat. Nos. 3,297,445 and 3,379,529 and West German Patent Application (OLS) No. 2,417,914.

Two or more different kinds of the above-described couplers can be each incorporated into the same layer of the photosensitive element. On the other hand, the same coupler can be incorporated into two or more different layers of the photosensitive element.

The coupler can be incorporated into a silver halide photographic emulsion layer in a known manner, for example, using methods as disclosed in U.S. Pat. No. 2,322,027:

(1) A method comprising the steps of dissolving the coupler in an organic solvent which is difficultly miscible with water and, in addition, has a high boiling point (about 170° C. or higher) such as an alkyl phthalate (e.g., dibutylphthalate, dioctylphthalate, etc.), a phosphate ester (e.g., diphenylphosphate, triphenylphosphate, tricresylphosphate, dioctylbutylphosphate, etc.), a citrate (e.g., tributyl acetylcitrate, etc.), a benzoate (e.g., octylbenzoate, etc.), an alkylamide (e.g., diethyllaurylamide, etc.), or a phenol (e.g., p-n-nonylphenol, 2-methyl-4-n-octylphenol, etc.); and dispersing the thus-obtained coupler solution into an aqueous medium and then mixing the obtained dispersion and a photographic emulsion.

(2) A method comprising the steps of dissolving the coupler into an organic solvent relatively immiscible with water and having a low boiling point, dispersing the obtained coupler solution and then mixing the resultant dispersion and a photographic emulsion. Specific examples of organic solvents which are suitable for use in this method include ethyl acetate, cyclohexanone, β-n-butylethoxyethylacetate and the like.

(3) A method comprising the steps of dissolving the coupler into an organic solvent miscible with water and then adding the resultant coupler solution to a photographic emulsion. Organic solvents used in this method may be removed from the photographic emulsion during production of the photosensitive element or may be allowed to remain in the photographic emulsion layer. Specific examples of organic solvents which are suitable for use in this method include dimethylformamide, dimethylsulfoxide, N-methylpyrrolidone, glycerin, tetrahydrofuran, diethyleneglycol monoacetate, diacetone alcohol, acetonitrile, methyl isobutyl ketone and the like.

(4) A method comprising the steps of dissolving the coupler into an alkaline aqueous solution and then adding the resultant coupler solution to a photographic solution.

The organic solvents as used in the methods (1), (2) and (3) can be appropriately combined with each other or the organic solvents as used in the methods (3) and (4) can be mixed with each other, depending upon the solubility of the coupler which is used in the present invention. The aqueous medium in which a solution of the coupler in an organic solvent is dispersed can contain a hydrophilic high molecular weight material. Preferably the hydrophilic high molecular weight material is sufficiently compatible with a hydrophilic binder in the photographic emulsion with which the above-described coupler dispersion is mixed. A suitable hydrophilic high molecular weight material can be selected from the materials used as the binder of the photographic emulsion.

The dye image-forming coupler can be generally used in an amount of about $2 \times 10^{-3}$ mol to about $5 \times 10^{-1}$ mol, preferably $1 \times 10^{-2}$ mol to $5 \times 10^{-1}$ mol of the coupler per mol of silver in the photographic emulsion layer.

As the support which can be used for the photosensitive element of the present invention, a wide variety of well known photographic supports can be used, such as those of synthetic resins, for example, cellulose acetate, polycarbonate, polyethylene terephthalate and polystyrene, a baryta-coated paper, a polyethylene-laminated paper and a glass plate. A suitable coating amount of silver for each photographic layer employed is about 0.2 to about 4.0, preferably 0.5 to 1.5 g/m².

The hydrophilic colloid which is used for the photosensitive element of the present invention is a high molecular weight material which is capable of forming a thin coating layer and is developing solution-permeable. All photographic hydrophilic colloids long well known in the art can be used, such as gelatin, acylated gelatin, graft gelatin, polyvinyl alcohol, a polyacrylic acid salt, polyacrylamide, a partially hydrolyzed product of polyvinyl acetate, polyacrylamide modified by the Hoffmann reaction, a copolymer of acrylic acid, acrylamide and N-vinylimidazole, polyvinylpyrrolidone and sodium alginate.

The hydrophilic colloid layers, particularly the gelatin-containing layer of the color photosensitive element of the present invention, can be hardened using a variety of cross-linking agents. Suitable cross-linking agents include inorganic compounds, such as a chromium salt and a zirconium salt, and aldehyde type cross-linking agents, such as mucochloric acid and 2-phenoxy-3-chloromaleic aldehyde acid, as disclosed in Japanese Patent Publication No. 1872/71, and such can be often advantageously used in the present invention. In addition, non-aldehyde type cross-linking agents, such as a polyepoxy compound, as disclosed in Japanese Patent Publication No. 7133/59, a poly-(1-aziridinyl) compound as disclosed in Japanese Patent Publication No. 8780/62, and an active halogen compound as disclosed in U.S. Pat. Nos. 3,362,827 and 3,325,287, are advantageous in hardening the color photosensitive element of the present invention.

The silver halide photographic emulsion which is used for the photosensitive element of the present invention can be selected, depending upon the end-use of the photosensitive element, from a wide variety of photographic emulsions long well known to one skilled in the art. Specific examples of suitable silver halides include silver chloride, silver chlorobromide, silver bromide, silver chlorobromoiodide and the like. These photographic emulsions can be sensitized with a chemical sensitizing agent, such as a sulfur sensitizer, a gold sensitizer, a reduction sensitizer and the like. These photographic emulsions can be further stabilized with a slightly soluble silver salt-forming agent, such as a mercapto compound, e.g., 1-mercapto-5-phenyltetrazole, etc., and with a stabilizer, such as 5-methyl-6-oxy-1,3,4-triazaindolizine. In addition, the photographic emulsion can contain a sensitizing dye, such as a cyanine and a merocyanine. It is particularly preferred for the silver halide photographic emulsion to be a negative type (i.e., a surface latent image-forming type) emulsion. In addition, non-surface latent image-forming type photographic emulsions can be used, such as an internal latent image-forming type direct reversal emulsion containing an electron-trapping agent, or a solarization type direct reversal emulsion.

The photosensitive element of the present invention can be employed for many end-uses as, for example, a color positive film, a color print paper, a color negative film, a color reversal film and the like.

The color photosensitive element of the present invention can be image-wise exposed and then processed in accordance with a conventional processing to form a dye image. The processing comprises the main steps of color development, bleaching and fixing and the optional steps of washing, stabilizing and the like. Two or more of these steps can be combined together and consequently can be performed in a single bath, such as a bleach-fixing bath. Color development processing is conventionally performed in an alkaline solution containing an aromatic primary amine developing agent. Of aromatic primary amine developing agents, para-phenylenediamine type developing agents are representative. Specific examples of typical developing agents include 4-amino-3-ethoxy-N,N-diethylaniline, 4-amino-3,5-dimethyl-N,N-diethylaniline, 4-amino-3-methyl-N-ethyl-N-($\beta$-hydroxyethyl)aniline, 4-amino-3-methyl-N,N-diethylaniline, 4-amino-3-methyl-N-ethyl-N-($\beta$-methylsulfonamidoethyl)aniline, 4-amino-3-($\beta$-methylsulfonamidoethyl)-N,N-diethylaniline, 4-amino-N-ethyl-N-($\beta$-hydroxyethyl)aniline, 4-amino-N,N-diethylaniline, 4-amino-N-ethyl-N-$\omega$-sulfobutylaniline and the like. Suitable processing procedures and processing solutions which can be employed are disclosed, for example, in U.S. Pat. Nos. 3,996,055, 3,994,729 and 3,997,348.

The following examples are given to illustrate the invention in greater detail.

EXAMPLE 1

The following compounds were used in this example.

| Test Compound | Structural Formula |
|---|---|
| (1) | 2-Methyl-5-tert-octylhydroquinone |
| (Invention) | [structure] |
| (2) (Invention) | 2-Methyl-5-tert-hexylhydroquinone [structure] |
| (3) (Invention) | 2-Methyl-5-tert-amylhydroquinone [structure] |
| (4) (Invention) | 2-tert-Butyl-5-t-amylhydroquinone [structure] |
| (5) (Invention) | 2-tert-Butyl-5-tert-hexylhydroquinone [structure] |
| (6) (Invention) | 2-Methyl-5-(1'-methylcyclohexyl)-hydroquinone [structure] |
| Compound A (Comparison) | 2,5-Di-t-octylhydroquinone [structure] |
| Compound B (Comparison) | 2,6-Di-n-dodecylhydroquinone [structure] |
| Compound C | 2,5-Di-n-octylhydroquinone |

-continued

| Test Compound | Structural Formula |
|---|---|
| (Comparison) | |
| Compound D (Comparison) | 2-t-Octylhydroquinone |
| Compound E (Comparison) | 5-sec-Octadecyl-2-(2-sulfo-t-butyl)-hydroquinone (sodium salt) |

[Structures shown: 2,5-di-n-octylhydroquinone; 2-t-octylhydroquinone; 5-sec-C$_{18}$H$_{37}$-2-[C(CH$_3$)$_2$CH$_2$SO$_3$Na]-hydroquinone]

1 g of each of the above-described test compounds was added to 1 ml of tricresylphosphate, respectively, and then dissolved therein at 100° C. After that, the thus-obtained solution was maintained at 25° C. in order to measure time when deposition of the compound could be observed.

The results obtained are shown in the Table 1 below.

TABLE 1

| Compound | Time for Deposition |
|---|---|
| (1) | More than 24 hours |
| (2) | " |
| (3) | " |
| (4) | " |
| (5) | About 20 hours |
| (6) | More than 24 hours |
| (A) | About 2 hours |
| (B) | Less than 1 hour |
| (C) | " |
| (D) | " |
| (E) | " |

As is apparent from the results in Table 1 above, the compounds used in the present invention are each selectively superior to comparison compounds in terms of stability in a solution, and, consequently, do not cause defects in a photographic image due to a deposition of the compound.

EXAMPLE 2

The First Layer (lowermost layer) to the Sixth Layer (uppermost layer) shown in Table 2 were each applied onto a paper support, both surfaces of which had been laminated with polyethylene, in order to prepare a multilayer color photosensitive element as a control (Sample A).

TABLE 2

| | | |
|---|---|---|
| Sixth Layer (protective layer) | Gelatin | 1,500 mg/m² (coated amount) |
| Fifth Layer (red-sensitive layer) | Silver Chlorobromide Emulsion (silver bromide 50 mol%, silver 300 mg/m²) | |
| | Gelatin | 1,500 mg/m² |
| | Cyan Coupler *1 | 500 mg/m² |
| | Coupler Solvent *2 | 250 mg/m² |
| Fourth Layer (ultraviolet light absorbing layer) | Gelatin | 1,200 mg/m² |
| | Ultraviolet Light *3 Absorbing Agent | 1,000 mg/m² |
| | Ultraviolet Light *2 Absorbing Agent Solvent | 250 mg/m² |
| Third Layer (green-sensitive layer) | Silver Chlorobromide Emulsion (silver bromide 50 mol%, silver 450 mg/m²) | |
| | Gelatin | 1,500 mg/m² |
| | Magenta Coupler *4 | 400 mg/m² |
| | Coupler Solvent *5 | 200 mg/m² |
| Second Layer | Gelatin | 1,000 mg/m² |
| First Layer | Silver Chlorobromide Emulsion (silver bromide 80 mol%, silver 450 mg/m²) | |
| | Gelatin | 1,500 mg/m² |
| | Yellow Coupler *6 | 500 mg/m² |
| | Coupler Solvent *7 | 500 mg/m² |
| Support | Polyethylene-Laminated Paper | |

*1 Cyan Coupler: 2-[α-(2,4-Di-t-amylphenoxy)butanimido]-4,6-dichloro-5-methylphenol
*2 Coupler Solvent: Di-n-butylphthalate
*3 Ultraviolet Light Absorbing Agent: 2-(2-Hydroxy-3-sec-butyl-5-t-butylphenyl)-benzotriazole
*4 Magenta Coupler: 1-(2,4,6-Trichlorophenyl)-3-[2-chloro-5-tetradecanamido]anilino-2-pyrazolin-5-one
*5 Coupler Solvent: o-Cresylphosphate
*6 Yellow Coupler: α-Pivaloyl-α-[2,4-dioxo-5,5'-dimethyloxazolidine-3-yl]-2-chloro-5-[α-2,4-di-(t-amylphenoxy)butanamido]acetanilide
*7 Coupler Solvent: o-Dioctylbutylphosphate Samples B to L were each prepared in the same manner as for Sample A except that comparison compounds as described above and the above-described compounds used in the present invention were each dissolved into the coupler solvent in combination with the yellow coupler which was added to the first layer of Sample A and then a dispersion of the thus-formed coupler solution in a gelatin solution was each added to the first layer, respectively. The coated amount of the yellow coupler which was used in Samples B to L was the same as that of Sample A. Compound (A) was used in an amount of 2 wt% of the coupler and the other alkyl hydroquinones were each added to the first layer in a molar amount equivalent to that of Compound (A).

These samples were each exposed to blue light, green light and red light through a continuous wedge for 0.5 second, respectively, and then subjected to the following processings.

| Steps | Time | Temperature |
|---|---|---|
| Color Development | 3 min 30 sec | 31° C. |
| Bleach Fixing | 1 min 30 sec | 31° C. |
| Washing | 2 min | 31° C. |
| Drying | | |

The processing solutions used had the following formulations.

| Formulation of Color Developer | |
|---|---|
| Benzyl Alcohol | 15 ml |
| Sodium Sulfite | 5 g |
| Potassium Bromide | 0.5 g |
| Hydroxylamine Sulfate | 2.0 g |
| Sodium Carbonate | 30.0 g |
| Sodium Nitrilotriacetate | 2.0 g |
| 4-Amino-3-methyl-N-(β-methane- | 5.0 g |

| | -continued | |
|---|---|---|
| sulfonamido)ethyl-aniline | | |
| Water to make | | 1,000 ml |
| | | (pH 10.1) |
| Formulation of Bleach Fixing Solution | | |
| Ammonium Thiosulfate | | 105 g |
| Sodium Sulfite | | 2 g |
| Disodium Ethylenediaminetetraacetate | | 40 g |
| Sodium Carbonate (monohydrate) | | 5 g |
| Water to make | | 1,000 ml |
| | | (pH 7.0) |

The fog density (yellow density) at the unexposed portion and the relative sensitivity of the processed photosensitive elements were each measured. The results obtained are shown in Table 3 below.

TABLE 3

| Sample No. | Compound | Fog | Relative Sensitivity |
|---|---|---|---|
| A | None | 0.14 | 0.00 (standard) |
| B | (1) | 0.09 | −0.03 |
| C | (2) | 0.09 | −0.03 |
| D | (3) | 0.08 | −0.04 |
| E | (4) | 0.10 | −0.03 |
| F | (5) | 0.10 | −0.03 |
| G | (6) | 0.09 | −0.03 |
| H | (A) | 0.12 | −0.09 |
| I | (B) | 0.14 | −0.05 |
| J | (C) | 0.13 | −0.09 |
| K | (D) | 0.09 | −0.11 |
| L | (E) | 0.15 | −0.12 |

As is apparent from the results in Table 3 above, Compounds (1), (2), (3), (4), (5) and (6) used in the present invention are each selectively superior to the comparison compounds in terms of anti-color fogging effect and reduction in sensitization.

EXAMPLE 3

Processed Samples A to L obtained as described in Example 2 above were each exposed to xenon light in a fading apparatus for 100 hours, and subsequently the yellow densities at the exposed area, the initial densities of which had been each 1.0 prior to exposure to xenon light, were measured. The ratio of preservation of the dye image was determined using the following relationship.

Yellow Image Preservation Ratio =
$$\frac{\text{Yellow Density after Fading} - \text{Yellow Density at the Unexposed Area}}{\text{Initial Yellow Density (1.0)} - \text{Yellow Density at the Unexposed Area}}$$

The ratios of dye image preservation which were obtained are shown in Table 4 below.

TABLE 4

| Sample No. | Compound | Ratio of Yellow Dye Image Preservation for 100 Hours |
|---|---|---|
| A | None | 0.65 |
| B | (1) | 0.58 |
| C | (2) | 0.60 |
| D | (3) | 0.60 |
| E | (4) | 0.57 |
| F | (5) | 0.57 |
| G | (6) | 0.58 |
| H | (A) | 0.49 |
| I | (B) | 0.50 |
| J | (C) | 0.47 |
| K | (D) | 0.59 |
| L | (E) | 0.50 |

As is apparent from the results in Table 4 above, the incorporation of comparison alkyl hydroquinones except for Compound (D) seriously degrades the light fastness of the yellow dye image, however, the asymmetrical hydroquinones used in the present invention do not so seriously deteriorate the same.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element comprising a support having thereon a red-sensitive silver halide photographic emulsion layer containing a cyan color-forming coupler, a green-sensitive silver halide photographic emulsion layer containing a magenta color-forming coupler, a blue-sensitive silver halide photographic emulsion layer containing a yellow color-forming coupler and, optionally, one or more non-light-sensitive subsidiary layers, wherein said blue-sensitive silver halide photographic emulsion layer contains at least one asymmetrical hydroquinone compound selected from the group consisting of 2-methyl-5-tert-octylhydroquinone, 2-tert-butyl-5-tert-amylhydroquinone, 2-tert-butyl-5-tert-hexylhydroquinone, 2-methyl-5-tert-hexylhydroquinone, 2-methyl-5-tert-amylhydroquinone, 2-methyl-5-(1′-methylcyclohexyl)-hydroquinone, and precursors thereof wherein either or both hydroxyl groups thereof are modified with an acyl group represented by the formulae:

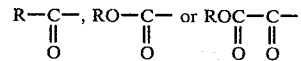

wherein R represents an alkyl group, said at least one asymmetrical hydroquinone compound serving to reduce color fogging without reducing the sensitivity and light fastness of a yellow dye image formed in said blue-sensitive silver halide photographic emulsion layer.

2. The color photographic light-sensitive element as set forth in claim 1, wherein said blue-sensitive silver halide photographic emulsion layer containing a yellow colorforming coupler, said green-sensitive silver halide photographic emulsion layer containing a magenta color-forming coupler and said red-sensitive silver halide photographic emulsion layer containing a cyan color-forming coupler are superimposed on said support in that order.

3. The color photographic light-sensitive element as set forth in claim 1, wherein said red-sensitive silver halide photographic emulsion layer containing a cyan color-forming coupler, said green-sensitive silver halide photographic emulsion layer containing a magenta color-forming coupler and said blue-sensitive silver halide photographic emulsion layer containing a yellow color-forming coupler are superimposed on said support in that order.

4. The color photographic light-sensitive element as set forth in claim 1, wherein said blue-sensitive silver halide photographic emulsion layer containing a yellow color-forming coupler, said red-sensitive silver halide photographic emulsion layer containing a cyan color-forming coupler and said green-sensitive silver halide photographic emulsion layer containing a magenta color-forming coupler are superimposed on said support in that order.

5. The color photographic light-sensitive element as set forth in claim 1, wherein said yellow color-forming coupler is a benzoylacetanilide type coupler or a pivaloylacetanilide type coupler.

6. The color photographic light-sensitive element as set forth in claim 5, wherein said yellow color-forming coupler is a two-equivalent coupler having a coupling-off group at the coupling position thereof selected from the group consisting of an acyloxy group, a sulfonyloxy group, an aryloxy group, a urethane group, an imido group, a hydantoinyl group, an oxazolidinedione group, a pyridine group and a pyridazone group.

7. The color photographic light-sensitive element as set forth in claim 5, wherein said yellow color-forming coupler is a two-equivalent coupler having a coupling-off group at the coupling position thereof selected from the group consisting of a phthalimido group, a succinimido group, a 5,5-dimethyl-3-hydantoinyl group and a 2,4-oxazolidinedione group.

8. The color photographic light-sensitive element as set forth in claim 5, wherein said pivaloylacetanilide type coupler is α-pivaloyl-α-(2,4-dioxo-5,5-dimethyloxazolidine-3-yl)-2-chloro-5-[α-2,4-di-(t-amylphenoxy)-butanamido]acetanilide.

9. The color photographic light-sensitive element as set forth in claim 1, wherein said hydroquinone compound is 2-methyl-5-tert-octylhydroquinone.

10. The color photographic light-sensitve element as set forth in claim 1, wherein the amount of said asymmetrical hydroquinone compound is about 0.1 to about 150 wt%, based on the weight of said yellow dye forming coupler.

11. The color photographic light-sensitive element as set forth in claim 1, wherein said R is an unsubstituted alkyl group.

* * * * *